(12) United States Patent
Hurowitz

(10) Patent No.: US 8,075,634 B2
(45) Date of Patent: Dec. 13, 2011

(54) ORTHOPEDIC DEVICE

(76) Inventor: Eli Hurowitz, Mountain Brook, AL (US)

(*) Notice: Subject to any disclaimer, the term of this patent is extended or adjusted under 35 U.S.C. 154(b) by 911 days.

(21) Appl. No.: 11/693,898

(22) Filed: Mar. 30, 2007

(65) Prior Publication Data

US 2007/0288097 A1 Dec. 13, 2007

Related U.S. Application Data

(60) Provisional application No. 60/790,828, filed on Apr. 11, 2006.

(51) Int. Cl.
*A61F 2/64* (2006.01)
(52) U.S. Cl. ........... 623/47; 623/48; 606/62; 606/329
(58) Field of Classification Search ........... 606/86 R, 606/89, 90, 96, 280, 281, 286, 329, 53.6–68; 623/47–56, 21.18, 20.32–20.34
See application file for complete search history.

(56) References Cited

U.S. PATENT DOCUMENTS

| | | | |
|---|---|---|---|
| 5,035,697 A | 7/1991 | Frigg | |
| 5,514,137 A * | 5/1996 | Coutts | ............................. 606/62 |
| 6,010,505 A | 1/2000 | Asche et al. | |
| 6,258,093 B1 | 7/2001 | Edwards et al. | |
| 6,547,791 B1 | 4/2003 | Buhren et al. | |
| 6,572,620 B1 | 6/2003 | Schon et al. | |
| 6,579,293 B1 | 6/2003 | Chandran | |
| 7,410,488 B2 * | 8/2008 | Janna et al. | ..................... 606/62 |
| 2002/0143337 A1 * | 10/2002 | Orbay et al. | .................... 606/69 |
| 2007/0162016 A1 * | 7/2007 | Matityahu | ....................... 606/69 |
| 2009/0182433 A1 * | 7/2009 | Reiley et al. | .............. 623/18.11 |

OTHER PUBLICATIONS http://ssepl.com (website), products including bone plates, nails, screws, and implants, Sharma Surgical & Engineering Pvt. Ltd. (last viewed Aug. 30, 2007).

* cited by examiner

*Primary Examiner* — Eduardo C Robert
*Assistant Examiner* — Christina Negrelli
(74) *Attorney, Agent, or Firm* — Steptoe & Johnson LLP

(57) ABSTRACT

An orthopedic device that includes an ankle arthrodesis nail having a bend, and a surgical implant kit for use in ankle arthrodesis in patients who suffer from severe bone defects in their ankles is provided. The invention further relates to a method of establishing ankle arthrodesis in a subject using an arthrodesis nail having a bend.

13 Claims, 3 Drawing Sheets

ORTHOPEDIC DEVICE

CLAIM FOR PRIORITY

This application claims priority under 35 U.S.C. §119(e) to U.S. Patent Application Ser. No. 60/790,828 filed on Apr. 11, 2006, which is hereby incorporated by reference.

TECHNICAL FIELD

This invention relates generally to an orthopedic device.

BACKGROUND

Some patients suffer from various conditions which require at least a portion of an ankle joint to be effectively immobilized. Such conditions include severe arthritis, infection and/or avascular necrosis of one or more bones in the region, congenital deformity of the tibio-talar or talocalcaneal joint or certain types of neuropathy. In all of these conditions, any motion of the bones relative to each other can cause severe pain in the foot or ankle to a point where a patient becomes effectively unable to walk or put any pressure on that foot. Accordingly, immobilization of the ankle joint becomes an option for the patient to begin walking without excruciating pain in the ankle and foot.

Immobilization of an ankle joint is usually done by inserting one or more rigid rods or pins into one or more bones in the ankle and in the hindfoot portion of the foot. This permanently affixes certain bones to other bones. The medical term for this type of permanent bone fixation is ankle arthrodesis. In a normal ankle joint, because of the placement of the bones, a straight rod which passes vertically through the calcaneus and into the tibia will normally pass through the talus.

SUMMARY

Rod and pin structures that have been developed for ankle arthrodesis can suffer from various limitations. Some patients who have had the old rod and pin devices inserted into their ankles have suffered from problems involving relative motion between the supposedly affixed tibial and calcaneal bones. This can lead to substantial pain in the affixed joint, and to instability when the patient is walking or standing. It can also lead to additional damage inside the joint, as the screws or other components rub and grind against one or more bones, which are often weakened and relatively soft in patients with severe joint or bone problems. Additionally the anatomic alignment of the hindfoot is not suited for the introduction of straight rod as there is a bend from the plantar portion of the calcaneus to the body of the talus and into the medullary canal of the tibia.

Accordingly, there is a need for an improved type of ankle arthrodesis assembly, which provides better and more stable and reliable fixation of the ankle and hindfoot in patients who need such treatment due to injury or disease of the foot or ankle.

A surgical implant and surgical implant kit, for use in ankle arthrodesis in patients who suffer from severe bone defects in their ankle, and a method of establishing ankle arthrodesis in a subject using an ankle arthrodesis nail having a bend is provided.

In one aspect, an ankle arthrodesis nail includes a rigid round tibio-talo-calcaneal rod having a distal portion and a proximal portion and a bend in the distal portion. The rod further includes proximal and distal holes for locking screws. The rod can have a bend in the proximal portion. The bend in the proximal portion and the bend in the distal portion can create an offset between the ends of the nail. The bend can be configured to match an anatomic alignment of a hindfoot. The bend can be at angle of between 5 and 20 degrees. The rod can have a diameter of between 10 to 13 mm. The rod can have a length of between 15 to 30 cm. The nail includes a rigid round tibio-talo-calcaneal rod having a bend in the distal portion and the rod further includes proximal and distal holes for locking screws.

In another aspect, a surgical implant kit includes an arthrodesis nail that includes a rigid round tibio-talo-calcaneal rod having a bend in the distal portion, the rod further including proximal and distal holes for locking screws, and posterior to anterior locking screws wherein the nail and the screws are configured to lock together to create a compression across ankle joints to aid in arthrodesis. The surgical implant kit can further include a precontoured guidewire to match the bend of the nail to provide a guide for reaming the opening for the insertion of the nail. The kit can also include a flexible reamer that is configured to pass over the guidewire. The kit can include a rod that has a bend in the proximal portion. The bend in the proximal portion and the bend in the distal portion can create an offset between the ends of the nail. The bend can be configured to match an anatomic alignment of a hindfoot. The bend can be at angle of between 5 to 20 degrees. The rod can have a diameter of between 10 to 13 mm. The rod can have a length of between 15 to 30 cm.

In another aspect, a method of establishing ankle arthrodesis in a subject, includes making an opening hole in the body of the calcaneus, talus and tibia, inserting an arthrodesis nail in the plantar portion of the heel from the calcaneus into the talus and tibia and locking the nail in the calcaneus bone with posterior to anterior locking screws to aid in arthrodesis. The method can further include using a guidewire to match the bend of the nail to provide a guide for reaming the opening for the insertion of the nail. The method can include using a flexible reamer to pass over the guidewire to open the tibial canal.

The details of one or more embodiments of the invention are set forth in the accompanying drawings and the description below. Other features, objects, and advantages of the invention will be apparent from the description and drawings, and from the claims.

DETAILED DESCRIPTION

Figure 1A:
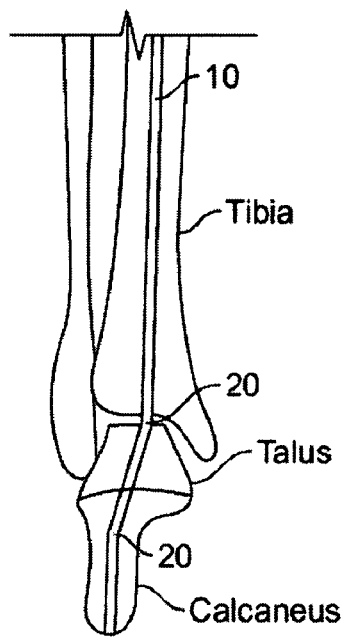
FIG. 1A is a schematic diagram depicting the posterior view of leg and foot showing the alignment of the hindfoot and the position of the arthrodesis nail having two bends within the hindfoot.
Figure 1B:
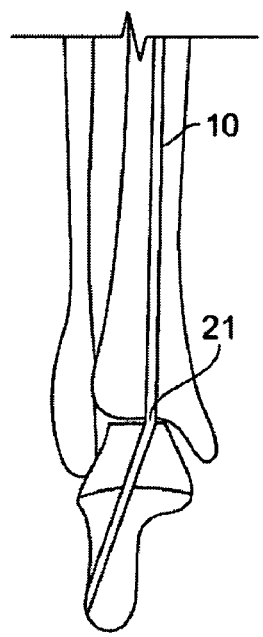
FIG. 1B is a schematic diagram depicting the posterior view of leg and foot showing the alignment of the hindfoot and the position of the arthrodesis nail having one bend within the hindfoot.

FIG. 1A depicts the bone structure and alignment of the hindfoot in a normal and healthy foot and further depicts an ankle arthrodesis nail 10 with a bend 20 that matches the anatomic alignment of the hindfoot. These bones include calcaneal bone, talus bone, and tibia bone. Previous designs of tibio-talo-calcaneal arthrodesis nail are straight and do not have bends to create an offset that matches the anatomic alignment of the hindfoot. Referring to FIG. 1A-B, the ankle arthrodesis nail 10 is a round rod in cross section that has one bend 21 or two bends 20 to create an offset to match the anatomy of the hindfoot.

Figure 2A:
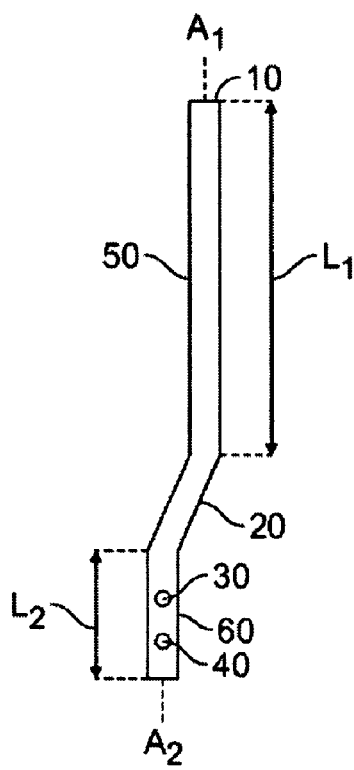
FIG. 2A is a schematic diagram showing the posterior view of the offset tibio-talo-calcaneal arthrodesis nail.
Figure 2B:
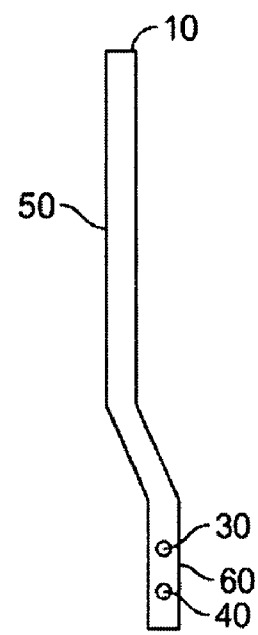
FIG. 2B is a schematic diagram showing the anterior view of the offset tibio-talo-calcaneal arthrodesis nail.
Figure 2C:
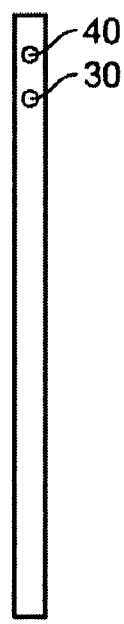
FIG. 2C is a schematic diagram showing the lateral view of the offset tibio-talo-calcaneal arthrodesis nail.

Referring to FIG. 2A-C, the rod has proximal 30 and distal holes 40 to accept locking screws. The rod can have a bend in the proximal portion. The rod can have a bend in the distal portion. The bend in the proximal portion and the bend in the distal portion can create an offset between the ends of the nail. The bend can be configured to match an anatomic alignment of a hindfoot. The bend can be at angle of between 5 to 20 degrees. The bend can be at angle of 15 degrees. The angle of the bend can be fixed during the manufacture of the nail.

Referring to FIG. 2A-B, the rod can have two bends where the long shaft 50 of the nail would be parallel with the short shaft 60 of the nail. Referring to FIG. 2A, an axis $A_1$ extending from the long shaft 50 would be parallel to the axis $A_2$ extending from the short shaft 60. The rod can have two bends of between 5 to 20 degrees each. The rod can have two bends of 10 degrees each. The rod can have a diameter of between 10 to 13 mm. The rod can have a length of between 15 to 30 cm. The ratio of the length of the long shaft L1 and the length of the short shaft L2, can be between 1:1 to 5:1. The lengths L1 and L2 can be configured to be proportionate to the size of the patient. The length of the long shaft L1 can be between 7.5 to 25 cm and the length of the short shaft L2 can be between 2.5 to 15 cm.

The dimensions for the rod and screw can vary in length or diameter, so that a range of devices having different sizes can be available for patients of different sizes. This will allow a surgeon to select and use two specific components that will work best in that specific patient, after the surgeon has analyzed the nature and severity of the damage, disease, or defect that requires surgical intervention. In one preferred approach, an assortment of vertical rods having lengths of between 15 to 30 cm can be provided, with diameters of between 9 to 14 mm. Oblique screws with lengths of between 5.5 to 7 cm, and diameters of between 4 to 7 mm, can be provided. These will allow surgeons to choose rod and screw combinations that will accommodate the majority of patients. If different sizes or angles are needed, they can be stocked by a manufacturer, or fabricated on a custom basis, preferably using computer controlled machining methods (such as laser cutting) to minimize the additional expenses of custom fabrication.

The rod and screw preferably should have beveled but not sharply-pointed tips. Screw tips can be provided with external threads, in at least a region which extends back about 1.5 cm or more from the tip. These threads should having a spacing and height which allow the threaded tip to securely engage, and pull against, the lower end of the tibial bone, as screw is tightened during surgical placement. Preferred dimensions (including the pitch, depth, and shape of the peaks) have been established for threaded screws that will be inserted into bones; those dimensional are well-known to companies that manufacture such surgical implants. Very fine threads are not used, since they can break and crumble bone material; instead, thread spacings of between 1.5 to 5 mm and a thread height (depth) of more than 1 mm are generally used.

In one embodiment, the rod can be inserted from the plantar portion of the heel by making an opening hole in the body of the calcaneus, talus and tibia. A guidewire with a similar offset or bend can be passed in a retrograde direction into the tibial canal. A guidewire that matches the bend of the nail can be used to provide guide for reaming the opening for the insertion of the nail. A reamer can then be passed over the pre-bent guidewire to shape or to open the tibial canal. The reamer can be a flexible reamer. Alternatively, any other appropriate drilling tool can be used to shape or enlarge the opening for the insertion of the nail. The nail can be passed from the calcaneus into the talus and then into the tibia and locked in the calcaneus bone with posterior to anterior screws. A force can be applied to the plantar surface of the foot, and the proximal portion of the nail locked to create compression across the joints to aid in arthrodesis.

Figure 3:
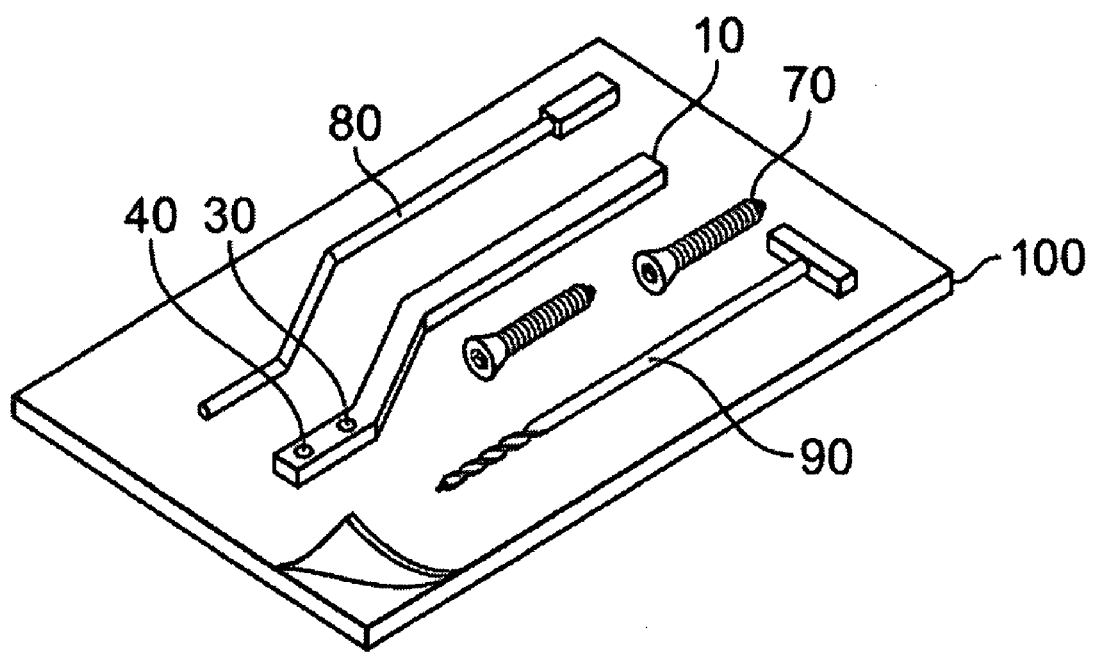
FIG. 3 is a schematic diagram showing a surgical implant kit in a sealable sterile package.

An ankle arthrodesis assembly can be created, inside an ankle joint, by a surgeon, using components that are contained in a kit that can be manufactured. In general, two classes of kits are anticipated. Referring to FIG. 3, a kit can contain a single set of components such as an arthrodesis nail 10 that includes a rigid round tibio-talo-calcaneal rod having a bend in the distal portion, the rod further including proximal 30 and distal holes 40 for locking screws, and posterior to anterior screws 70 wherein the nail and the screws are configured to lock together to create a compression across ankle joints to aid in arthrodesis. The surgical implant kit can further include a precontoured guidewire 80 to match the bend of the nail to provide a guide for reaming the opening for the insertion of the nail. The kit can further include a flexible reamer 90. Such a kit can be ordered by a surgeon, with the exact sizes of both main components fully specified, after the surgeon has analyzed the problems and needs of a specific patient. The kit may be enclosed in a sealed package 100 that maintains the sterility of the surgical implant components.

The second type of kit (which might be preferred by a hospital or orthopedic clinic where several surgeons work) can contain a variety of rods and screws, such as a plurality of rods of each desired length (such as 15, 20, and 25 cm) and a plurality of screws of each desired length (such as 5.5 to 7 cm). Such kits can include precontoured guidewires to match the bend of the nail to provide a guide for reaming the opening for the insertion of the nail. Such kits can further include flexible reamers that can be passed over the pre bent guide wire to open the tibial canal. This will allow a surgeon to select a preferred combination for any specific patient, from among the assortment that is already available at that clinic or hospital.

In general, surgical kits typically enclose any and all implantable components within sealed enclosures that maintain sterility. The implantable components may be made from stainless steel, titanium or any other appropriate material suitable for implantation. However, it should be noted that any implanted components disclosed herein can be easily sterilized immediately before use, by autoclaving or similar means.

A number of embodiments of the invention have been described. Nevertheless, it will be understood that various modifications may be made without departing from the spirit and scope of the invention. Accordingly, other embodiments are within the scope of the following claims.

What is claimed is:
1. An ankle arthrodesis nail, comprising:
 a rigid round tibio-talo-calcaneal rod having a distal portion and a proximal portion, a bend in the distal portion, wherein the bend is configured to match an anatomic alignment of a hindfoot, the rod further comprising proximal and distal holes for locking screws, wherein the rod has a bend in the proximal portion, wherein the bend in the proximal portion and the bend in the distal portion create an offset between the ends of the nail.

2. The nail of claim 1, wherein the bend is at angle of between 5 to 20 degrees.

3. The nail of claim 1, wherein the rod has a diameter of between 10 to 13 mm.

4. The nail of claim 1, wherein the rod has a length of between 15 to 30 cm.

5. A method of establishing ankle arthrodesis in a subject, comprising:
   making an opening hole in the body of the calcaneus, talus and tibia;
   inserting an arthrodesis nail in the plantar portion of the heel from the calcaneus into the talus and tibia, the nail comprising a rigid round tibio-talo-calcaneal rod having a bend in the distal portion, wherein the bend is configured to match an anatomic alignment of a hindfoot of the subject, and the rod further comprising proximal and distal holes for locking screws; and
   locking the nail in the calcaneus bone with posterior to anterior locking screws to aid in arthrodesis.

6. The method of claim 5, further comprising using a guidewire to match the bend of the nail to provide a guide for reaming the opening for the insertion of the nail into a tibial canal.

7. The method of claim 6, further comprising using a flexible reamer to pass over the guidewire to open the tibial canal.

8. The method of claim 5, wherein the rod has a bend in the proximal portion, wherein the bend in the proximal portion and the bend in the distal portion create an offset between the ends of the nail.

9. A surgical implant kit comprising:
   an arthrodesis nail comprising a rigid round tibio-talo-calcaneal rod having a bend in the distal portion, wherein the bend is configured to match an anatomic alignment of a hindfoot, the rod further comprising proximal and distal holes for locking screws; and
   posterior to anterior locking screws; and
   a precontoured guidewire to match the bend of the nail to provide a guide for reaming the opening for the insertion of the nail,
   wherein the nail and the screws are configured to lock together to create a compression across ankle joints to aid in arthrodesis, wherein the rod has a bend in the proximal portion, wherein the bend in the proximal portion and the bend in the distal portion create an offset between the ends of the nail.

10. The surgical implant kit of claim 9, further comprising a flexible reamer that is configured to pass over the guidewire.

11. The surgical implant kit of claim 9, wherein the bend is at angle of between 5 to 20 degrees.

12. The surgical implant kit of claim 9, wherein the rod has a diameter of between 10 to 13 mm.

13. The surgical implant kit of claim 9, wherein the rod has a length of between 15 to 30 cm.

* * * * *